US010835237B2

(12) United States Patent
Dey

(10) Patent No.: US 10,835,237 B2
(45) Date of Patent: Nov. 17, 2020

(54) PACKAGE FOR SUTURES

(71) Applicant: DS-Technology GmbH, Winnenden (DE)

(72) Inventor: Clifford Dey, Allmersbach im Tal (DE)

(73) Assignee: DS-TECHNOLOGY GMBH, Winnenden (DE)

( * ) Notice: Subject to any disclaimer, the term of this patent is extended or adjusted under 35 U.S.C. 154(b) by 394 days.

(21) Appl. No.: 15/751,257

(22) PCT Filed: Apr. 24, 2017

(86) PCT No.: PCT/EP2017/000509
§ 371 (c)(1),
(2) Date: Feb. 8, 2018

(87) PCT Pub. No.: WO2018/196940
PCT Pub. Date: Nov. 1, 2018

(65) Prior Publication Data
US 2020/0197007 A1   Jun. 25, 2020

(51) Int. Cl.
*A61B 17/06* (2006.01)
*A61B 17/00* (2006.01)

(52) U.S. Cl.
CPC .......... *A61B 17/06133* (2013.01); *A61B 2017/00902* (2013.01); *A61B 2017/00955* (2013.01); *A61B 2017/06142* (2013.01)

(58) Field of Classification Search
CPC ... A61B 17/00; A61B 17/06; A61B 17/06133; A61B 17/90; A61B 2017/00902; A61B 2017/00955; A61B 2017/06142
(Continued)

(56) References Cited

U.S. PATENT DOCUMENTS 4,961,498 A   10/1990   Kalinski et al.
4,967,902 A   11/1990   Sobel et al.
(Continued)

FOREIGN PATENT DOCUMENTS

EP   2 172 157 A1   4/2010
EP   2286733 A1   2/2011
(Continued)

OTHER PUBLICATIONS

International Search Report of PCT/EP2017/000509, dated Aug. 31, 2017.
(Continued)

*Primary Examiner* — Bryon P Gehman
(74) *Attorney, Agent, or Firm* — Collard & Roe, P.C.

(57) ABSTRACT

A package for surgical sutures has a base member, an outer wall extending upwardly form the periphery of the base member, a plurality of pyramidal shaped standoff members arranged in an oval shape and a flat suture channel cover member having a plurality of precision holes to lock the cover member to the standoff members of the base member. The inner surface of the outer wall of the base member is a profiled surface and the outer periphery of the cover member has a profiled surface corresponding to the profiled surface of the outer wall of the base member. The profiled surface of the outer wall can consist of a plurality of D shaped vertical members extending from the top surface of the base member to the top of the outer wall.

18 Claims, 4 Drawing Sheets

(58) Field of Classification Search
USPC .............................. 206/63.3, 339, 380–382
See application file for complete search history.

(56) References Cited

U.S. PATENT DOCUMENTS

| | | | |
|---|---|---|---|
| 5,131,533 A | | 7/1992 | Alpern |
| 5,180,053 A | | 1/1993 | Cascio et al. |
| 5,230,424 A | | 7/1993 | Alpern et al. |
| 5,655,652 A | * | 8/1997 | Sobel ............... A61B 17/06133 206/63.3 |
| 5,799,788 A | * | 9/1998 | Webb ............... A61B 17/06161 206/380 |
| 6,047,815 A | * | 4/2000 | Cerwin ............ A61B 17/06133 206/63.3 |
| 6,135,272 A | | 10/2000 | Sobel et al. |
| 7,637,369 B2 | * | 12/2009 | Kennedy .......... A61B 17/06133 206/63.3 |
| 8,011,499 B2 | | 9/2011 | McHugh Karow et al. |
| 2006/0226031 A1 | | 10/2006 | Kennedy et al. |

FOREIGN PATENT DOCUMENTS

| | | |
|---|---|---|
| EP | 2 389 119 A1 | 11/2011 |
| EP | 3 095 392 A1 | 11/2016 |
| WO | 2013/049400 A1 | 4/2013 |

OTHER PUBLICATIONS

Written Opinion of the International Searching Authority of PCT/EP2017/000509, dated Aug. 31, 2017.

\* cited by examiner

PACKAGE FOR SUTURES

CROSS REFERENCE TO RELATED APPLICATIONS

This application is the National Stage of PCT/EP2017/000509 filed on Apr. 24, 2017. The international application under PCT article 21(2) was published in English.

TECHNICAL FIELD

This invention relates to packages for surgical sutures. Conventional surgical suture and needle packages serve several useful functions, including protecting the needles and sutures during handling, shipping, and storage. In addition, the packages facilitate access and release of the needles and sutures during surgery or other medical procedures prior to application. The packages may be used for surgical sutures armed with surgical needles or for unarmed surgical sutures without needles.

PRIOR ART

Packaging for surgical sutures with or without needles is well known in the art. There are two types of packages that have been conventionally used for surgical needles and sutures. One type of package is a paper folder package wherein a medical grade paperboard is folded and cut into a plurality of panels. The suture is then wound onto a panel, and the package is then assembled by first folding the panels into a desired configuration, and then locking the panels in place using slits and locking tabs which have been cut into the panels.

Another type of suture package which has been used is a tray package having a winding channel. These tray packages typically have an oval shape with outer and inner walls forming an oval winding channel. The packages are typically moulded from plastics. The packages are mounted onto a winding fixture and sutures are then wound into the winding channel. Suture packages typically have a needle park member for mounting and securing a surgical needle if a surgical needle is mounted to the sutures. Conventional needle parks can consist of foam members, or equivalent retention structures. The needle park members can also be utilized for mounting one end of a suture wound into the winding channel.

U.S. Pat. No. 4,961,498 discloses a two-piece suture package having an oval winding channel. U.S. Pat. No. 4,967,902 discloses a one-piece channel suture package having a plurality of door members which retain the suture in the channel. U.S. Pat. No. 5,230,424 discloses a package having a substantially square shape and having a square shaped suture channel wherein a plurality of cantilevered doors are mounted to an inner wall to maintain sutures in the channel. U.S. Pat. No. 5,655,652 discloses a package having an oval-shaped winding channel with a top friction plate member in lieu of doors or cantilevered doors.

U.S. Pat. No. 5,131,533 discloses a needle park having a hinged section. U.S. Pat. No. 5,180,053 discloses a suture package having a cantilevered arm needle park. This park extends vertical to the base of the package. This type of park has the disadvantage of allowing the needle to release if the package is flexed during transportation.

U.S. Pat. No. 6,135,272 discloses a plurality of cantilevered cover door members with spaces in between. These door members have a disadvantage of deforming if the stylus is moving at a high speed therefore limiting the winding speed.

WO 2013/049400 A1 discloses a suture package having two halves. The interior of the body portion is provided with a pair of posts in one half of the body portion and a corresponding pair of mating bosses in the other half of the body portion. When the two halves of the base are pressed together, the posts fit into the bosses in a press fit or snap fit manner to secure the two halves together. The posts and bosses also provide a structure around which the suture strands may be wrapped.

EP 2 172 157 A1 discloses a suture package for retaining a barbed suture including a suture retaining member with an outer wall and an inner wall. The inner wall is radially spaced from the outer wall and defines a suture retaining area therebetween. The outer wall includes a plurality of inwardly extending tabs configured to engage a cover. The suture package further includes a cover configured to be received within the outer wall of the suture retaining member and to selectively engage the inwardly extending tabs formed thereon.

EP 3 095 392 A1 discloses a package for sutures having a winding channel created by having an outside wall and an inner row of cylindrical standoff members to form a channel for sutures. The package has a base member and a flat cover ember that is mounted to the base member by a plurality of snap locks located on top of the cylindrical standoff members. The edge of the base member has cover locking tabs along the outside wall.

Although the suture tray packages of the prior art are adequate and effective for their intended use, there are disadvantages associated with such packages. An example of one type of problem which may occur is suture "hang-up" when the surgeon attempts to withdraw the suture from the package. Accordingly, there is a need in this art for novel suture tray packages having winding channels which are readily adaptable to high-speed packaging processes which overcome the disadvantages of the prior art packages, including problems associated with suture withdrawal. Accordingly there is a need for gasses to be able to flow easily around the sutures to facilitate sterilization and antimicrobial coating.

SUMMARY OF THE INVENTION

Proceeding from this previously known prior art, it is an object of the present invention to provide a novel tray package having a winding channel which is useful in a high-speed packaging process for packaging surgical sutures.

It is also an object of the present invention to provide a tray package with the ability to securely maintain sutures in the channel that has an open interior wall to facilitate application of sterilization and/or antibacterial application.

It is still yet a further object of the present invention to provide a novel suture tray package which facilitates withdrawal of sutures from the package.

It is still yet a further object of the invention to provide a novel needle park to provide better retention of the needles during handling.

The suture package according to the invention is produced by the features of the main claim. Appropriate developments of the invention are subject matter of further claims following the main claim.

Accordingly, a suture package is disclosed. The package has a base member having a top surface, a bottom surface, an outer periphery and a longitudinal axis. An outer wall extends upwardly about the periphery of said base member, said outer wall having an inner surface, an outer surface, and a top. An inner plurality of pyramidal shaped standoff members is arranged in an oval shape that defines and captures the suture therefore forming a channel for the suture to lie in.

There is also a flat paper suture channel cover member for mounting to the base member. The suture channel cover member has a top surface, a bottom surface and an outer periphery. A plurality of precision holes exists in the cover member to lock said cover member to the standoff members of the base member. A port exit opening having a first end and a second end is located in the outer track wall and forms a suture port.

Needle park mean are located interior to the standoff members from the top surface of the base member.

The cover member is mounted to the base member to form the package of the present invention by aligning the cover member fastener holes with the base member standoff members and inserting the tops of the standoff members into the precision holes in the cover member. The standoff members can be deformed by using ultrasonic sound, for example. This flattens and broadens the top of the standoff members, thereby preventing the cover member to slip from the standoff members. This forms a suture channel between the inner surface of the outer wall of the base member, the top surface of the base member, the outer side of the standoff members and the bottom surface of the suture cover member.

An optional plastic top suture cover may be utilized to complete the assembled package. This assembly is completed after the suture is wound into the channel formed by the cover member, the outer wall of the base member, the top surface of the base member and the standoff members.

These and other features and advantages of the present invention will become more apparent from the following description and accompanying drawings.

The profiled surface of the outer wall may consist of a plurality of bulges extending from the top surface of the base member to the top of the outer wall. Those bulges may be D shaped vertical members. The length of the D shaped vertical members may vary in one package. The D shaped vertical members should protrude at least one millimetre from the outer wall of the base member in order to provide an interlocking barrier that will contain sutures down to a size of 10/0 and keep them within the package.

The package may comprise a plurality of air slots in the suture track area of the base member. In this case, a plurality of lock members extending inward form the inner surface of the outer wall may exist. Those lock members can be located directly above the air slots so the whole base member may be produced in one mould. The cover member of the package can be positioned under those lock members in order to fasten the cover member to the base member. Alternatively or additionally, there may be at least one tab member extending outward form the outer surface of the standoff member and facing the inner surface of the outer wall. Those tab members can also be located directly above the air slots of the base member. The cover member of the package can be positioned above the at least one tab member in order to better define the distance between the cover member and the top surface of the base member. Furthermore, those tab members can prevent the suture from leaving the suture track area once the cover member is removed.

There may be at least one spacer extending from the inner surface of the base member, each spacer having a top, a bottom and an outer surface, said spacers being arranged between two standoff members. Said spacers in conjunction with each other and in conjunction with at least some of the standoff members may form an inner wall for the suture track area.

The standoff members of the base member may be shaped like truncated pyramids.

The base member may be transparent. This enables the user of the package to better see the location of the suture and the needle. Furthermore, the kind of suture and needle can be seen through the transparent base member.

The cover member may comprise holes for receiving the winding pins.

The package may already comprise a suture wound into the winding channel and a surgical needle mounted in the needle park means.

The package may have an oval configuration.

The needle park members may comprise at least one cantilevered horizontal arm extending from the top surface of the base member and a retaining feature for fixing the needle under the at least one horizontal arm of the needle park member. The retaining feature may comprise a concave area at the bottom side of the at least one horizontal arm and at least one snap at the top surface of the base member.

Additionally or alternatively, the needle park members may comprise at least one first web and at least one second web aligning each other. The ends of the first and the second end, which are facing each other, can be formed as a clamping device. For example, the end of the first web, facing the second web, may comprise a concave area and the end of the second web, facing the first web, may comprise a convex area.

Further advantages and features of the invention can be gathered from the features which are further specified in the claims and from the following exemplary embodiments.

BRIEF DESCRIPTION OF THE DRAWINGS

In the following text, the invention will be described and explained in greater detail using the exemplary embodiments which are shown in the drawings.

DESCRIPTION OF THE PREFERRED EMBODIMENT

Figure 1:
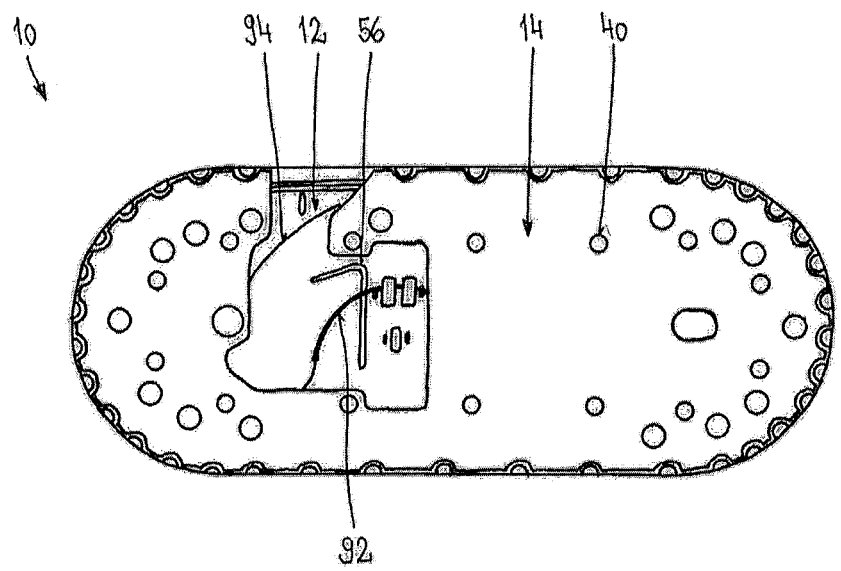
FIG. 1 is a top, plan view of a first embodiment of the package having a needle with suture mounted therein.
Figure 6:
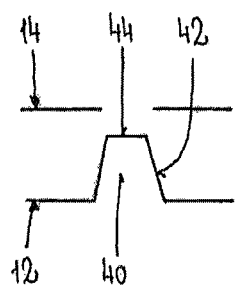
FIG. 6 is a cross section through one of the standoff members before the cover member has been fixed to it.
Figure 7:
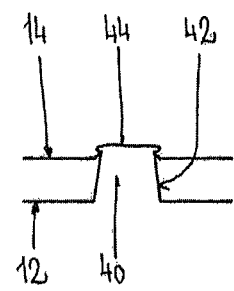
FIG. 7 is a cross section through the standoff member of FIG. 6 after the cover member has been fixed to it.

The package 10 according to a first embodiment of the present invention is illustrated in FIGS. 1 to 7. As seen in FIGS. 1, 6, and 7, the package 10 has a base member 12 and a flat suture channel cover member 14.

Figure 2:
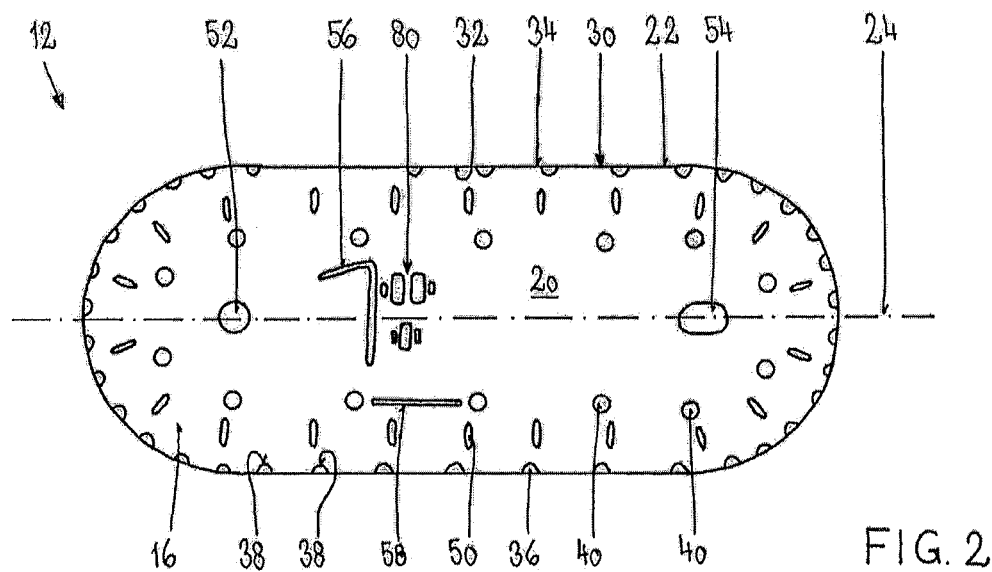
FIG. 2 is a top view of the base member of the package in FIG. 1.

Referring now in more detail to FIG. 2, the base member 12 is seen to have a top surface 20 and a bottom surface. The base member 12 is also seen to have an outer periphery 22. The base member 12 is seen to be a substantially flat and substantially oval shaped member having a longitudinal axis 24. However, although it is desired that the base member 12 along with the package 10 be oval shaped, other configurations can be used including circular, polygonal, square with rounded corner, and the like and combinations thereof and equivalents thereof.

Extending upwardly about the periphery 22 of the base member 12 is an outer wall 30. Outer wall 30 is seen to have a bottom, an inner surface 32, an outer surface 34 and a top 36. The inner surface 32 of the outer wall 30 is a profiled surface having a plurality of D shaped bulges 38 extending from the top surface 20 of the base member 12 to the top 36 of the outer wall 30. The D shaped bulges 38 protrude from the outer wall 30 at a minimum of one millimetre.

There can be optional notches at the top of the outer wall 30 of the base member 12. Theses notches are there to keep the base member 12 flat.

In FIG. 2 the standoff members 40 are seen to extend upward from the top surface 20 of the base member 12. According to FIG. 6 the standoff members 40 have a pyramidal shaped outer surface 42 and flat tops 44. The tops 44 of the standoff members 40 are preferably flush with the top 36 of the outer wall 30.

Extending through the bottom of the base member 12 is a plurality of air slots 50 (see FIG. 2). The air slots 50 are located between the outer wall 30 and the standoff members 40. Also extending through the bottom of the base member 12 are the circular winding drive pin locating hole 52 and the oval drive pin locating hole 54. The holes 52 and 54 are seen to be disposed along the longitudinal axis 24 and are at opposite ends of the base member 12. An optional slit in the bottom of the base member 12 interior to the outer wall 30 can form the tab lifting member 56.

Furthermore, there is a cantilevered spacer 58 positioned between two of the standoff members. The spacer 58 defines the position when the cover member 14 is pushed down onto the base member 12 to the lowest possible level. There can be one spacer 58 as shown in FIG. 2 or there can be more spacers 58 evenly spread on the top surface 20 of the base member 12.

Figure 3:
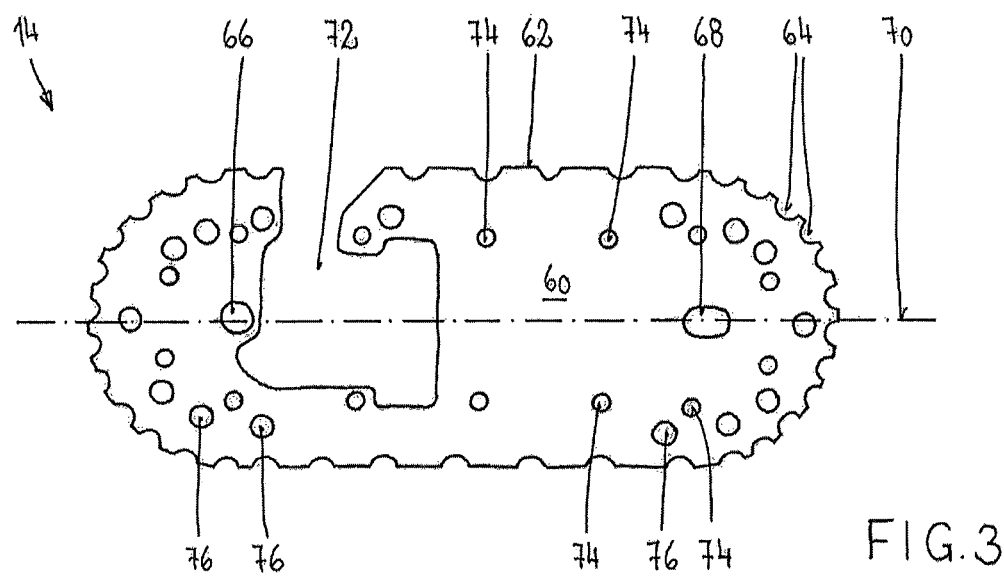
FIG. 3 is a top view of the cover member of the package in FIG. 1.

Referring now to FIG. 3, the suture channel cover member 14 is seen to be illustrated. The suture channel cover member 14 has a top surface 60, a bottom surface, and a periphery 62. The D shaped bulges 38 of the outer wall 30 of the base member have a mirrored cut in the outer periphery 62 of the cover member 14. Those matching indentations 64 in the cover member 14 provide—when assembled—an interlocking barrier that will contain sutures down to a size of 10/0 and keep them within the package 10.

The pin winding holes 66 and 68 are seen to be contained at opposite ends of the cover member 14. The pin winding holes 66 and 68 are seen to extend through the cover member 14 and to be disposed in the cover member 14 along its longitudinal axis 70, toward either end. They line up with the winding drive pin holes 52, 54 in the base member 12. Pin winding hole 66 is circular in shape, whereas pin winding hole 68 is of oval shape. However, other geometric shapes can be utilized.

The suture exit port 72 is seen to be contained in the cover member 14. Also seen to extend through the cover member 14 are precision holes 74 that mate up with the standoff members 40 of the base member 12. The diameter and shape of the precision holes 74 is determined by the shape of the standoff members 40. In order to lock the cover member 14 to the base member 12 the top 44 of the standoff members 40 are deformed by using ultrasonic sound, for example. This flattens and broadens the top 44 of the standoff members 40 (see FIG. 7). After this deformation of the top 40 of the standoff members 40, the precision holes 74 of the cover member cannot slip off the standoff members 40 so the cover member 14 is securely locked to the base member 12.

There is a multiplicity of suture winding pin holes 76 that extend through the cover member 14. The suture winding pin holes 76 are located between the outer periphery 62 and the precision holes 74. The preferred shape of the suture winding pin holes 76 is circular but other shapes can be utilized such as oval, octagonal, semi-circular, polygonal, triangular, combinations thereof and equivalents thereof and the like.

Figure 4:
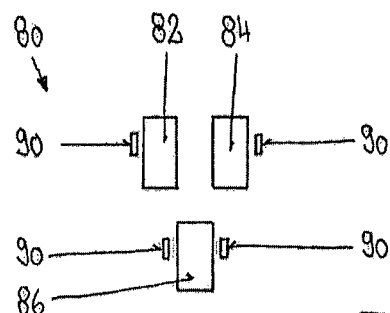
FIG. 4 is an enlarged view of the base member of the package in FIG. 1 showing the needle park means.
Figure 5:
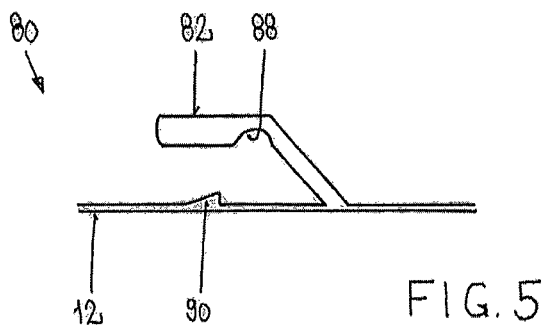
FIG. 5 is a cross section through one of the needle park means of FIG. 4.

To maintain the control of the small needles a novel needle park 80 in the base member 12 is shown. The needle park 80 in FIGS. 4 and 5 is shown in its preferred configuration with three horizontal cantilevered arms 82, 84, 86. Each horizontal arm 82, 84, 86 has a concave area 88 at its bottom side (see FIG. 5). There are snaps 90 in the form of angled ramps on either side of the horizontal cantilevered arms 82, 84, 86 rising from the top surface 20 of the base member 12. These ramps 90 prevent the smaller needles from moving during transportation or from premature releasing.

The packages 10 of the present invention are assembled in the following manner. The needle 92 is placed into at least one of the horizontal cantilevered arms 82, 84, 86 of the needle park. Then, the suture 94 is threaded into the winding channel 16 of the base member 12 between the inner surface 32 of the outer wall 30 and the standoff members 40. During winding, negative pressure is applied through the air slots 50 in order to keep the suture 94 in the winding channel 16. Next, the suture channel cover member 12 is printed by conventional means and pin winding holes 66, 68 of the cover member 14 are aligned with winding drive pin locating holes 52, 54 of the base member 12. After the winding of the suture 94 is completed, the cover member 14 is pushed down onto the base member 12 until the precision holes 74 are in contact with the outer surface 42 of the standoff members 40. While still applying negative pressure, the tops 44 of the standoff members 40 are deformed in order to lock the cover member 14 to the base member 12.

The package 10 containing the wound suture 94 and the needle 92 may then be placed in a conventional pouch or package for conventional sterilization treatments such as gaseous sterilants, autoclaving, radiation and the like.

Figure 9:
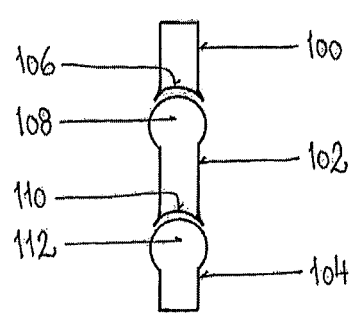
FIG. 9 is an enlarged view of the base member in FIG. 8 showing the needle park means.
Figure 8:
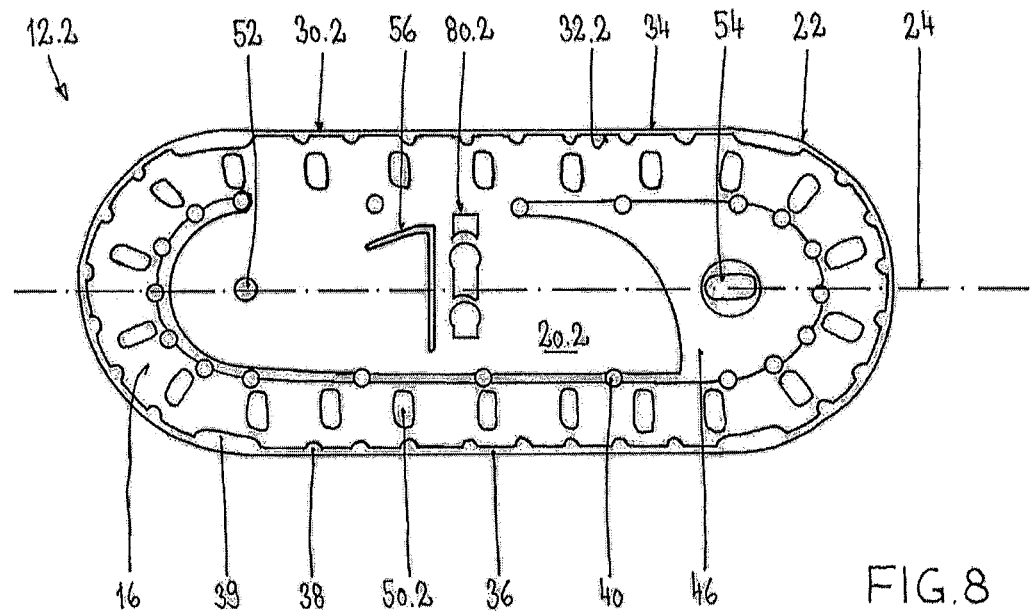
FIG. 8 is a top view of the base member of a second embodiment of the package.

The base member 12.2 of a package according to a second embodiment of the present invention is illustrated in FIGS. 8 and 9. The base member 12.2 as seen in FIG. 8 can be combined with a cover member similar to the cover member 12 shown in FIG. 3.

The base member 12.2 is seen to have a top surface 20.2 and a bottom surface. The base member 12.2 is also seen to have an outer periphery 22.

The base member 12.2 is seen to be a substantially flat and substantially oval shaped member having a longitudinal axis 24.

Extending upwardly about the periphery 22 of the base member 12.2 is an outer wall 30.2. The inner surface 32.2 of the outer wall 30.2 is a profiled surface having a plurality of D shaped bulges 38, 39 extending from the top surface 20.2 of the base member 12.2 to the top 36 of the outer wall 30.2.

The D shaped bulges 38, 39 protrude from the outer wall 30.2 at a minimum of one millimetre. The D shaped bulges 38 are approximately semi-circular in shape whereas the D shaped bulges 39 are much longer. In FIG. 8 the four D shaped bulges 39 are positioned in the transition region of the base member 12.2 between the straight middle section and the round end section. In contrast to that, it is possible to have more or less of the longer D shaped bulges 39 and they could be positioned at will.

In FIG. 8 the standoff members 40 are seen to extend upward from the top surface 20.2 of the base member 12.2. The standoff members 40 have a pyramidal shaped outer surface 42 and flat tops 44. The tops 44 of the standoff members 40 are preferably flush with the top 36 of the outer wall 30.2. Most of the standoff members 40 are part of an inner wall area 46.

The top of the inner wall area 46 lies beneath the top 36 of the outer wall 30.2 and also beneath the top 44 of the standoff members 40. Therefore, the inner wall area 46 can define the position when the cover member is pushed down onto the base member 12.2 to the lowest possible level. Furthermore, the inner wall area 46 can ease the withdrawal of the suture.

Extending through the bottom of the base member 12.2 is a plurality of air slots 50.2. The air slots 50.2 are located between the outer wall 30.2 and the inner wall area 46 with the standoff members 40. The air slots 50.2 are located in the suture track channel 16. Also extending through the bottom of the base member 12.2 are the circular winding drive pin locating hole 52 and the oval drive pin locating hole 54. The oval drive pin locating hole 54 also extends through the inner wall area 46 of the base member 12.2. The holes 52 and 54 are seen to be disposed along the longitudinal axis 24 and are at opposite ends of the base member 12.2. An optional slit in the bottom of the base member 12.2 interior to the inner wall area 46 can form the tab lifting member 56.

To facilitate the insertion of the needles a novel needle park 80.2 in the base member 12.2 is shown. The needle park 80.2 in FIG. 9 is shown in its preferred configuration with a first web 100, a second web 102, and a third web 104 aligning each other. The web 100 comprises a concave area 106 on the end facing the second web 102. The second web 102 comprises a convex area 108 on the end facing the first web 100 and a concave area 110 on the end facing the third web 104. The third web 104 comprises a convex area 112 on the end facing the second web 102. The convex areas 108, 112 of one web 102, 104 and the corresponding concave areas 106, 110 of the respective web 100, 102 form a clamping device for a needle 92. The needle 92 can be positioned between the concave area 106, 110 and the convex area 108, 112 in order to be fixed in the package.

It is possible to have a combination of the needle park 80 according to FIGS. 4 and 5 and the needle park 80.2 according to FIG. 9 in one base member. For example, the needle park 80.2 according to FIG. 9 could be combined with one horizontal cantilevered arm 86 and two angled ramps on either side of the horizontal cantilevered arm 86 according to FIG. 4.

Figure 10:
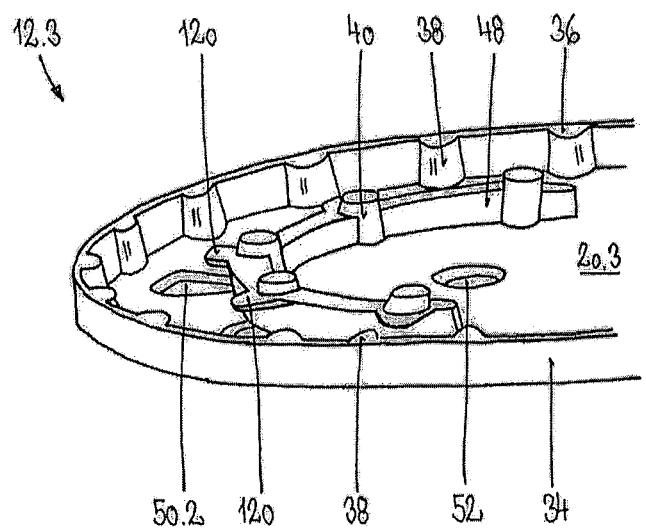
FIG. 10 is an enlarged perspective view of a part of the base member of a third embodiment of the package.

The base member 12.3 of a package according to a third embodiment of the present invention is illustrated in FIG. 10. The base member 12.3 as seen in FIG. 10 can be combined with a cover member similar to the cover member 12 shown in FIG. 3.

The base member 12.3 is seen to have a top surface 20.3 and a bottom surface. The base member 12.3 is also seen to have an outer periphery 22. The base member 12.3 is seen to be a substantially flat and substantially oval shaped member having a longitudinal axis 24. Extending upwardly about the periphery 22 of the base member 12.3 is an outer wall 30. The outer wall 30 of the base member 12.3 is identical to the outer wall 30 of the base member 12 according to FIGS. 1 and 2. It would also be possible to combine the outer wall 30.2 of the base member 12.2 according to FIG. 8 with the base member 12.3 according to FIG. 10.

In FIG. 10 the standoff members 40 are seen to extend upward from the top surface 20.3 of the base member 12.3. The standoff members 40 have a pyramidal shaped outer surface 42 and flat tops 44. The tops 44 of the standoff members 40 are preferably flush with the top 36 of the outer wall 30. The standoff members 40 positioned at the round end section of the base member 12.3 are part of an inner wall 48. The top of the inner wall 48 lies beneath the top 36 of the outer wall 30.2 and also beneath the top 44 of the standoff members 40. Therefore, the inner wall 48 can define the position when the cover member is pushed down onto the base member 12.3 to the lowest possible level. Furthermore, the inner wall 48 can ease the withdrawal of the suture.

Extending through the bottom of the base member 12.3 is a plurality of air slots 50.2. The air slots 50.2 are located between the outer wall 30.2 and the inner wall 48 with the standoff members 40. The air slots 50.2 are located in the suture track channel 16. Extending outward from the outer surface 42 of the standoff members 40 are tab members 120. The tab members 120 are facing the inner surface 32 of the outer wall 30. The tab members 120 are positioned above the air slots 50.2 so the whole base member 12.3 may be produced in one mould. A cover member can be positioned above the tab members 120 in order to better define the distance between the cover member and the top surface 20.3 of the base member 12.3. Furthermore, those tab members 120 can prevent the suture from leaving the suture track area 16 once the cover member is removed.

In contrast to the embodiment shown in FIG. 10, those tab members 120 could also be combined with standoff members 40 without an inner wall 48 (as shown in FIGS. 1 and 2) or with standoff members 40 included in an inner wall area 46 (as shown in FIG. 8).

There could be lock members extending inward from the inner surface of the outer wall of the base member. Those lock members should also be positioned above the air slots of the base member so the whole base member may be produced in one mould. A cover member of the package can be positioned under those lock members in order to fasten the cover member to the base member. Those lock members could be combined with the tab members of the standoff members and they could also be combined with the different D shaped vertical members 38, 39 as shown in FIG. 8.

The base member 12 of the packages 10 of the present invention may be manufactured from conventional mouldable materials. It is especially preferred to use polyolefin materials such as polyethylene and polypropylene, other thermoplastic materials, and polyester materials such as nylon, and equivalents thereof. Preferably, the base members 12 of the present invention are injection moulded, however, the base members 12 may be formed by other conventional processes and equivalents thereof included thermo-forming. If desired, the packages 10 may be manufactured as individual assemblies or components which are then assembled.

The sutures and needles that can be packaged in the packages 10 of the present invention include conventional surgical needles and conventional bio-absorbable and nonabsorbable surgical sutures and equivalents thereof. The packages 10 of the present invention are useful to package small diameter sutures which were previously difficult to package in tray packages because of removal or hang-up problems upon withdrawal of such sutures from the packages. These problems have been overcome using the packages 10 of the present invention.

The invention claimed is:

1. A package for surgical sutures, comprising
a base member having a top surface, a bottom surface, an outer periphery and a longitudinal axis,
an outer wall extending upwardly from the periphery of said base member, said outer wall having an inner surface, an outer surface and a top,
a plurality of pyramidal shaped standoff members arranged in an oval shape that defines and captures a respective suture of the sutures extending from the inner surface of the base member, each standoff member having a top, a bottom and an outer surface said standoff members in conjunction with each other form a suture track area to retain the respective suture of the sutures,
a flat suture channel cover member having a top surface, a bottom surface and an outer periphery,
said cover member having a plurality of precision holes to lock said cover member to the standoff members of the base member,
an opening in the outer edge of the cover member forming a suture port having a first end and a second end,
a needle park member located interior to the standoff members and extending from the top surface of the base member wherein
the inner surface of the outer wall of the base member is a profiled surface,
the outer periphery of the cover member has a profiled surface corresponding to the profiled surface of the outer wall of the base member.

2. The package according to claim 1 wherein
the profiled surface of the outer wall consists of a plurality of bulges extending from the top surface of the base member to the top of the outer wall.

3. The package according to claim 2 wherein
the bulges are D shaped vertical members.

4. The package according to claim 3 wherein
the D shaped vertical members protrude at least one millimetre from the outer wall of the base member.

5. The package according to claim 1 further comprising
a plurality of air slots in the suture track area of the base member.

6. The package according to claim 5 further comprising
a plurality of lock members extending inward from the inner surface of the outer wall, each lock member having a top, a bottom and an outer surface.

7. The package according to claim 5 further comprising
at least one tab member extending outward from the outer surface of each of the standoff members and facing the inner surface of the outer wall.

8. The package according to claim 1 further comprising
at least one spacer extending from the inner surface of the base member and having a top, a bottom and an outer surface, said at least one spacer being arranged between two standoff members.

9. The package according to claim 8 wherein
said spacers in conjunction with each other and in conjunction with at least some of the standoff members form an inner wall for the suture track area.

10. The package according to claim 1 wherein
the standoff members of the base member are shaped like truncated pyramids.

11. The package according to claim 1 wherein
the base member is transparent.

12. The package according to claim 1 additionally comprising
holes through the cover member for receiving winding pins.

13. The package according to claim 1, wherein the suture track area comprises a winding channel, the package further comprising
a suture wound into the winding channel,
a surgical needle mounted in the needle park member.

14. The package according to claim 13 wherein
the needle park member comprises at least one cantilevered horizontal arm extending from the top surface of the base member and a retaining feature for fixing the needle under the at least one horizontal arm of the needle park member.

15. The package according to claim 14 wherein
the retaining feature comprises a concave area at the bottom side of the at least one horizontal arm and at least one snap at the top surface of the base member.

16. The package according to claim 1 wherein
the package has an oval configuration.

17. The package according to claim 1 wherein
the needle park member comprises at least one first web and at least one second web aligning each other
the ends of the first web and the second web, which are facing each other, are formed as a clamping device.

18. The package according to claim 17 wherein
the end of the first web, facing the second web, comprises a concave area
the end of the second web facing the first web, comprises a convex area.

* * * * *